United States Patent
Brown

(10) Patent No.: US 6,290,681 B1
(45) Date of Patent: *Sep. 18, 2001

(54) FLOW MONITORING DEVICE FOR MEDICAL APPLICATION

(75) Inventor: Eric W. Brown, Newport Beach, CA (US)

(73) Assignee: Remote Medical Corporation, Newport Beach, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 08/507,122

(22) Filed: Jul. 26, 1995

Related U.S. Application Data

(63) Continuation-in-part of application No. 08/360,994, filed on Dec. 20, 1994, now Pat. No. 5,445,622.

(51) Int. Cl.[7] ............................................. A61M 5/00
(52) U.S. Cl. ..................... 604/246; 604/65; 128/DIG. 13
(58) Field of Search .................................. 604/246, 247, 604/65–67, 207, 118, 131, 250–254; 128/DIG. 12, DIG. 13

(56) References Cited

U.S. PATENT DOCUMENTS

| | | | |
|---|---|---|---|
| 4,261,388 | * 4/1981 | Shelton ................................. | 604/253 |
| 4,452,273 | * 6/1984 | Hanzawa et al. ..................... | 604/253 |
| 4,652,262 | * 3/1987 | Veracchi ............................... | 604/250 |
| 4,680,977 | * 7/1987 | Conero et al. ........................ | 604/253 |
| 4,827,970 | * 5/1989 | Sugisaki et al. ...................... | 604/250 |
| 5,267,980 | * 12/1993 | Dirr, Jr. et al. ....................... | 604/253 |
| 5,445,622 | * 8/1995 | Brown .................................. | 604/246 |

* cited by examiner

*Primary Examiner*—Manuel Mendez
(74) *Attorney, Agent, or Firm*—Gene Scott-Patent Law & Venture Group

(57) ABSTRACT

An intravenous system for monitoring the flow of IV fluids to a patient is embodied in a wristwatch sized case for placement on the patient. The device includes a switch uses capable of detecting when flow starts or stops. In one embodiment, the range of flow rates which may trigger a signal is increased using a plurality of sensor elements. The flow indicator switch uses a conical fluid conducting means with a movable stem body which reacts to the motion of the IV fluid. A signal-emitter-sensor arrangement provides a means for converting physical displacement into an electrical signal indicating displacement of the movable member thus detecting when flow starts and stops, as well as the rate of flow. Collected information is stored in a data storage means and may be either displayed on a display means housed within the case, or alternately, the collected data may be uploaded to a computer.

18 Claims, 7 Drawing Sheets

FLOW MONITORING DEVICE FOR MEDICAL APPLICATION

This application is a continuation in part of application Ser. No. 08/360,994, filed Dec. 20, 1994, now U.S. Pat. No. 5,445,622.

FIELD OF THE INVENTION

This invention relates to intravenous (IV) fluid delivery systems and in particular to a monitoring device for providing information on when and if the delivery of an IV fluid to a patient actually occurred.

BACKGROUND OF THE INVENTION

The rapid rise of health care costs has become an important issue in modern society. To help reduce the costs, professional care givers have begun to seek alternatives, one of which is home health care services. These services not only tend to reduce costs, but are also preferred by the patient wishing to remain in his familiar environment. Among the many types of services provided are: respiratory care, rehabilitation therapy, cardiac monitoring procedures, and infusion therapy.

Infusion therapy involves IV administration of drugs. Making this therapy safe and convenient for a home situation allows a great number of patients who would otherwise be hospitalized to remain at home and still receive medication. Currently, over 300,000 patients annually use a home infusion therapy delivery system. Typically, patients include the elderly with chronic diseases like cancer, patients with either Crohns disease, HIV or other immune system disorders, and patients suffering from chronic pain. Many of these patients require infusion treatment over a long duration such as months or even years.

One characteristic of home IV drug therapy, in contrast to hospital administered therapy, is that a nurse is not always present or readily available. To provide safe and effective treatment, home infusion therapy usually requires that the patient himself, or other non-professional caregiver, such as a relative, administer IV fluids. Special training is required because many home care patients on IV therapy require multiple drugs or multiple doses of the same drug each day. The average nursing visit to a home infusion therapy patient is typically about 90 minutes including commuting time. The typical patient gets between 1 and 4 nursing visits per week, but has to take IV medications daily. Since the cost of daily care by a nurse is not usually covered by most insurers, the cost of attention by a nurse is most economically applied in training the patent or other amateur caregiver and in monitoring the therapy program.

In the home care situation non-compliance, over-medication or under-compliance with the IV therapy protocol is a serious issue and quite prevalent. For instance, non-compliance (not taking a medication) or under-compliance (taking fewer or smaller dosages than prescribed) occurs in up to approximately one-third to one-half of elderly home therapy patients. Typical compliance related problems include forgetting to follow the specified procedure for administration of the IV medication, forgetting to turn on the various devices used to administer the IV medication and forgetting to turn off a medical device which then delivers too much medication (over-medication). Reasons for compliance related problems are varied and include poor communication, confusion or forgetfulness regarding the procedures and/or equipment, or even attempts to avoid the adverse side effects of IV medications and fluids. Misapplication of the home IV therapy protocol can have serious ramifications resulting in greatly increased home health care nursing expenses, re-hospitalization, and reduction in health status of the patient. Thus, there is a strong need for improved monitoring of patient compliance with the health care program. Benefits of such improved monitoring and compliance include, but are not limited to, improved health at a lower cost, while still remaining in the preferred home environment.

To properly monitor compliance with an IV therapy protocol, a device may be provided for monitoring the flow of IV medications and fluids. The IV fluids for a single patient are likely to come from several different sources or systems including IV pumps, IV fluid controllers, gravity drips, syringes, and other devices.

A typical gravity powered IV may be as simple as an IV bag hanging on a pole in which a nurse or care giver manually adjusts a valve to limit the flow rate, but not control it accurately, or it may use an electronic controller which optically counts the drops of fluid as they pass an optical sensor and then adjusts the flow rate accordingly. However, optical drop counting sensors only provides an indication that the fluid is flowing past the sensor when in a vertical orientation such as hanging from an IV pole. Thus the patient and IV delivery equipment must remain relatively stationary during the administration of the medication or fluid. Optical drop counters also function poorly at higher flow rates and higher line pressures, such as when a syringe is used, because the fluid moving past the drop counter tends to become a continuous stream rather than remaining discrete drops. Therefore, the optical drop counter technique cannot be adapted for use with all fluid sources.

An alternative to an optical drop counting sensor, or as a stand-alone measuring device, is a single point pressure transducer to measure the fluid pressure in the IV tubing at a selected point of measurement. This type of sensor is common in IV pumps and is used to indicate that the pump is generating a static pressure head and, correspondingly, causing fluid flow or backpressure in the event of an occlusion in the IV line. This type of sensor only determines line pressure at the selected point, and is only useful in monitoring the pressure caused by the IV pumping device and the related backpressure caused by moving fluids into the patient's body. However, this type of single-point pressure sensor is useful in many IV delivery systems to determine if fluid pressures are at correct levels, and to detect changes in fluid pressure which are indicative of an occluded or collapsed vein. Often, when a certain threshold pressure is detected in a device using this type of sensor, an alarm is sounded to warn of a flow problem. This type of device measures changes in the static line pressure of a fluid line, but is unable to determine if a patient is following proper IV drug administration procedures and cannot differentiate between changes in pressure due to fluid flow versus some other cause, such as an occlusion in which there is actually no fluid flow.

Increased backpressure in an IV fluid line causes problems, and, as described above, many IV fluid delivery systems use a sensor to determine when high backpressure develops, i.e., greater than a few inches of water, for instance when an infiltration of tissue occurs or the tubing becomes occluded. Upon the detection of a significant backpressure, the device sounds an alarm and may function to automatically discontinue the delivery of the IV medication and fluids. Therefore, it is important that any device used to monitor whether or not fluid is flowing does not cause a substantial increase in backpressure or a false occlusion alarm might be triggered.

Other alternatives use indirect methods to monitor the flow of IV fluids. For instance, the speed and number of rotations in a pump mechanism may be monitored to indirectly determine when fluid flow is occuring. This is useful for flows caused by an IV pump, but is of no value to patients who also receive gravity drips or fluids via syringe. Since nearly all infusion therapy patients must perform venous access device maintenance procedures, such as a heparin flush via syringe to maintain the patency of their IV lines, this pump rotation technique is not of value for monitoring all infusions.

The time usage for an IV delivery system may be recorded to prepare bills to patients. Typically, the information is printed or stored in an electronic memory device such as the electronic controls for the drop counter or IV pump. The information may be used to determine which of several patients are using the IV system being monitored, it may be used to coordinate several IV delivery systems with a centrally managed pump, or it may be used to facilitate billing and reimbursement. Unfortunately, none of these systems accommodate tracking of fluid delivered from a variety of sources such as to a patient who receives syringes, gravity drips, and IV pump infusions. The present invention provides an improved flow indicator switch, which overcomes the above-mentioned limitations of the prior art.

SUMMARY OF THE DISCLOSURE

The present invention is an IV system which provides certain monitoring advantages. An electronic data processing and storage device is used in conjunction with a unique flow indicator switch to record events in the IV infusion process. The processor may be connected in real time or may be used simply as a data recorder for later analysis. If used in real time the processing device is used to interpret signals related to IV flow, to provide instructions on how to properly sense whether fluid flow is occurring, and on when to inform the user to use the IV system or even to take other medications, vis-a-vis, oral or injection therapy, etc.

In the preferred embodiment of the present invention, an IV infusion system provides a switch body conducting means having a movable stem body indicator to monitor a flow of fluid through a fluid flow path. The flow indicator includes a switch having a movable stem body that is forced to move by direct viscous forces against it within the flow path, so that it moves in the direction of fluid flow. The movable stem body can sense a change in system flow including positive flow startup from stagnation in order to indicate that fluid flow has stopped or started. A signal emitter-sensor means preferably including an infrared emitter and detector sense the change of position of the movable switch member. A spring element provides a restoring force to return the movable switch member to a null position indicating "no flow" when fluid flow has ceased. The force exerted by the spring element is adjusted to sense flow rates as low as 3.0 milliliters per hour.

Further, the conducting means has a variable orifice positioned in a shaped fluid passageway in the form of an annulus. The orifice changes in cross-sectional size depending upon the position of the movable stem body. The cross-sectional area of the orifice is designed to enhance sensitivity to low fluid flows when the orifice has a smaller cross-sectional area, as well as to limit backpressure generated by higher fluid flow when the orifice has a larger cross-sectional area. In the preferred embodiment, the increase in backpressure is limited to about 4 inches of water with flow rates as high as 3600 milliliters per hour. In the preferred embodiment, the flow indicator switch functions equally well at line pressures from a fraction of an inch of water to over 60 pounds per square inch pressure because no occlusion of the flowpath occurs. Therefore, the flow indicator switch is not an occlusive device and does not react to changes in static pressure.

The processor is preferably operationally coupled to the flow indicator switch, to monitor the time and date of starts and stops of IV fluid flow in the system. One preferred embodiment of the present invention provides for the processor to be housed in a case about the size of a wrist watch so that it is highly portable for wearing on the person. This provides several key advantages and benefits to the infusion patient which would not otherwise become possible.

The processor and the flow indicator may be operationally coupled by fluid conduits, electrical conductors, wireless transmitters and receivers, or the like. The processor includes a memory storage device which retains information related to the programmed IV protocol and the actual time of start and stop events. The processor may of course be interconnected with a computer or other high speed data device for data archiving purposes and for further data analysis. In the preferred embodiment, the processor is serially coupled with a notebook PC that downloads prescribed IV protocols and uploads actual fluid flow start/stop events for comparison. The downloaded and uploaded data may include fluid flow events from any or all sources of fluid including, but not limited to, IV pumps, gravity drips, and syringes.

The flow indicator switch may operate in any attitude providing an advantage over prior apparatus. Moreover, the flow indicator switch housing is formed with a fluid flow path that is easily de-aired by a flow of fluid through the device housing. The flow indicator switch is a passive device, in which the movable switch member is actuated by the fluid flow through the tube. It can have a sensitivity to low fluid flows of less than or equal to 3.0 milliliters per hour and a backpressure limited to less than or equal to 4.0 inch of water line pressure at higher flow rates common to intravenous drug therapy, such as 3600 milliliters per hour. The flow indicator switch can work well with pulsed fluid flows without triggering a false alarm in the fluid delivery equipment.

Another advantage is that the small size and portability of the flow indicator switch precludes the necessity of having the patient attach and detach the device each time it is used. It may be attached to the patient's IV catheter for long periods of time. Also, since it is a passive device, it requires less electrical power and maintenance, thereby reducing health care costs. It may be connected to a catheter or IV tubes by standard connectors typically used on common IV equipment, or it may be an integral part of the IV catheter tube assembly.

Other features and advantages of the invention will become apparent from the following detailed description, taken in conjunction with the accompanying drawings which illustrate, by way of example, various features of the several embodiments of the invention.

BRIEF DESCRIPTION OF THE DRAWINGS

A detailed description of embodiments of the invention will be made with reference to the accompanying drawings, wherein like numerals designate corresponding parts in the several figures, in such drawings.

DETAILED DESCRIPTION OF THE PREFERRED EMBODIMENTS

Figure 1:
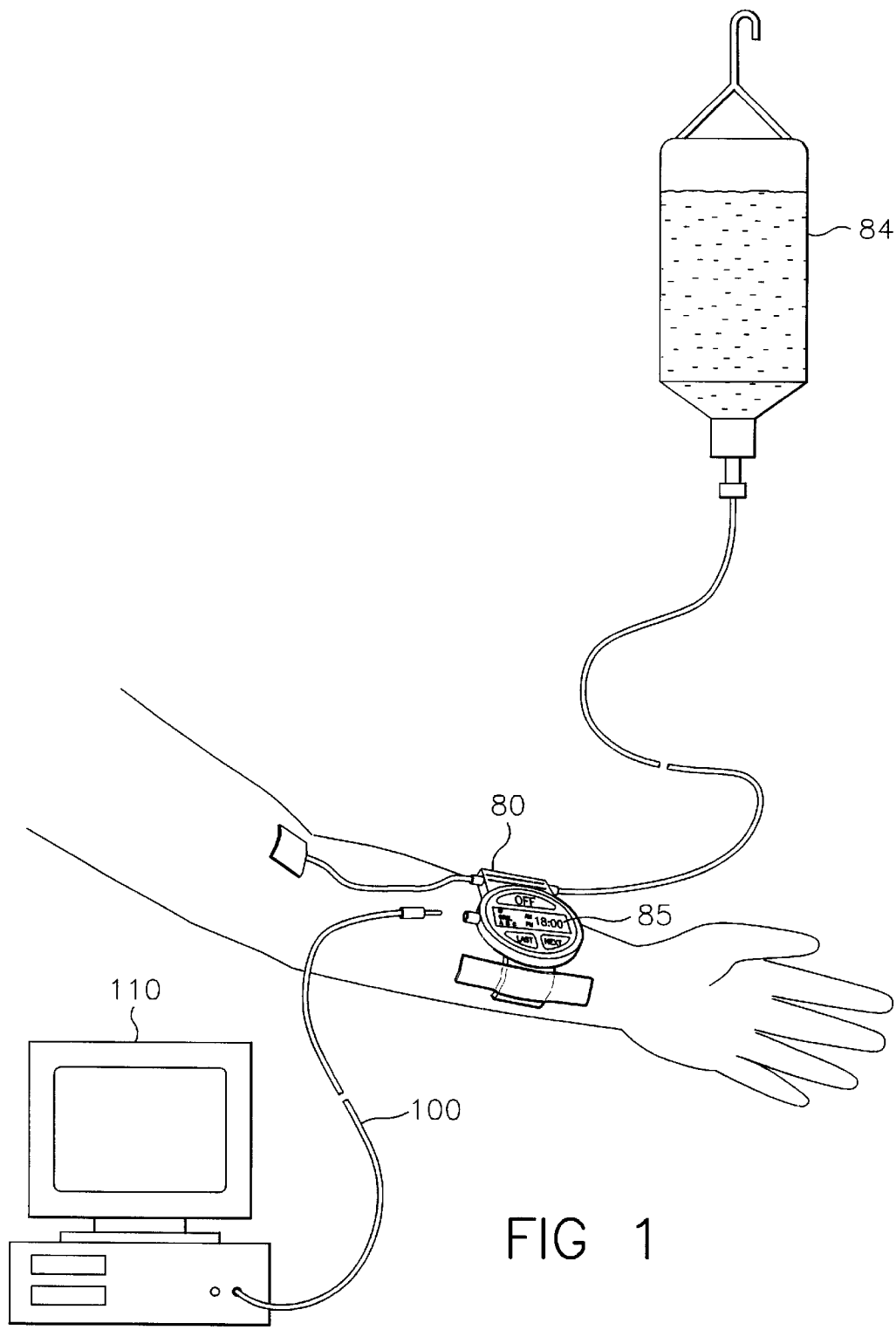
FIG. 1 particularly showing a signal emitter-sensor means and fluid conducting means with a stem body in a first position against a proximal shoulder is a perspective view showing on overview of the present invention in a general orientation as applied to a patient in a wrist or arm mounted embodiment.
Figure 5:
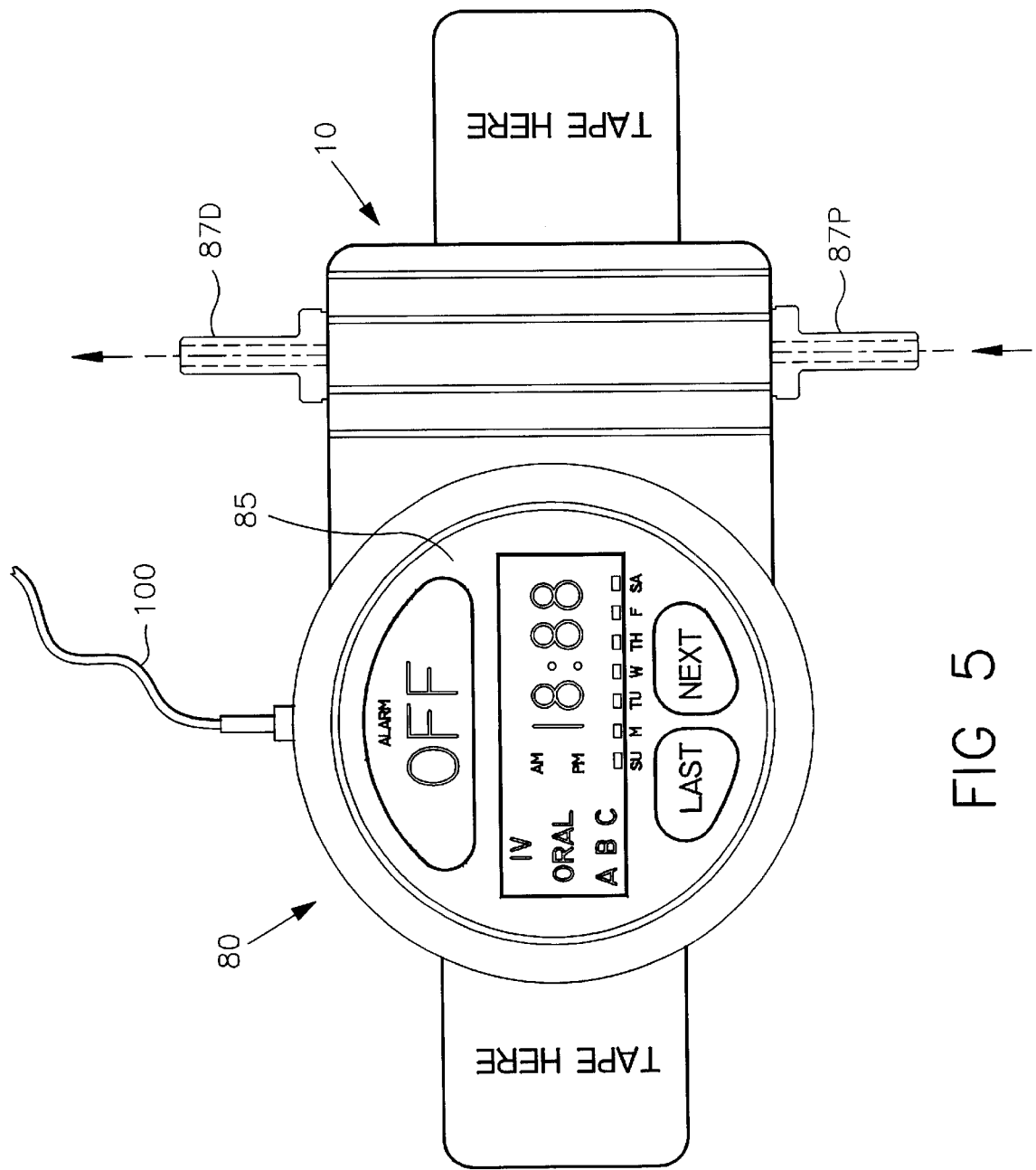
FIG. 5 is a view of the preferred layout of the face of a wrist watch sized event monitor housing of the invention.

FIG. 1 shows a fluid flow device for monitoring the flow of a fluid such as is used in medical applications such as infusion therapy where an IV fluid is monitored for providing information on the delivery of the IV fluid to a patient. Other fluids, and other applications both within medicine and outside of the medical field may be suitable for advantageously applying the device. Preferably, the device has a wristwatch sized case 80 that attaches to a patient's arm or that may be taped to the patient's chest depending upon the site of the IV catheter. The case 80 provides a visual display means 85 that is easily viewed by the patient. As shown more clearly in FIG. 5, the display 85 preferably displays a variety of different pertinent information such as the current time and date; the time and date of the next IV infusion process including which drugs to use; and the time and date of the last IV infusion process performed.

The monitoring apparatus for the intravenous fluid delivery is a system comprised of two primary components, the first being a processor circuit 60 housed within the case -80, used to store and record electronic data pertaining to fluid flow. The second component is a signal emitter-sensor means 52, for detecting fluid stop and start events as well as potentially monitoring of fluid flow rate.

Figure 2:
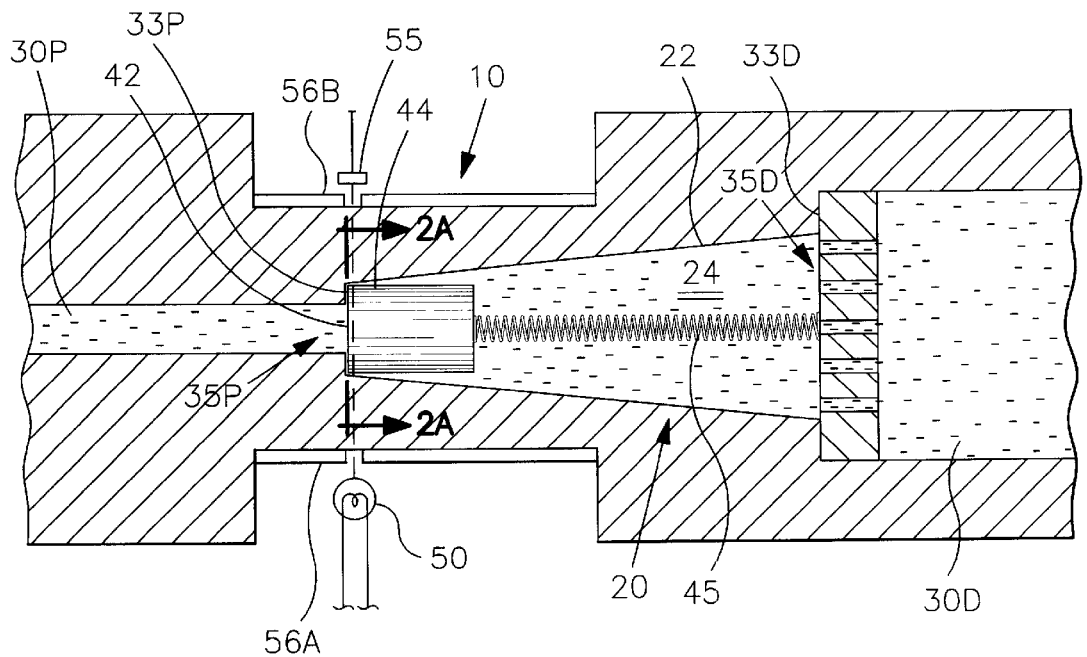
FIG. 2 is a schematic representation of a first prefered embodiment of the present invention of FIG. 1 shown as the simple flow indicator switch held within the case shown in FIG. 1, wherein some dimensions are shown exaggerated for better understanding of the principles involved, and particularly showing a flow conduit, inlet and outlet orifices, stem body, and light emitter and detector of the preferred embodiment.
Figure 2A:
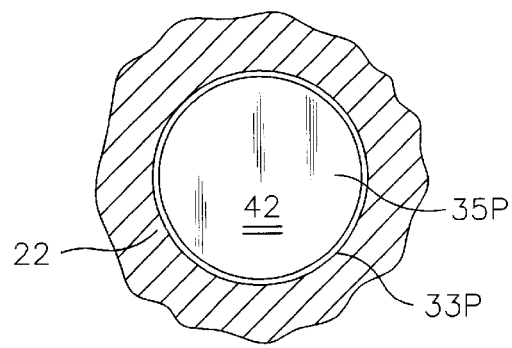
FIG. 2A is a cross-section view of the flow indicator switch taken along lines 2A—2A of FIG. 2 and particularly showing the preferred relationship between a proximal shoulder, the fluid conductor and an end of the stem body, wherein some dimensions are shown exaggerated for better understanding of the principles.
Figure 2B:
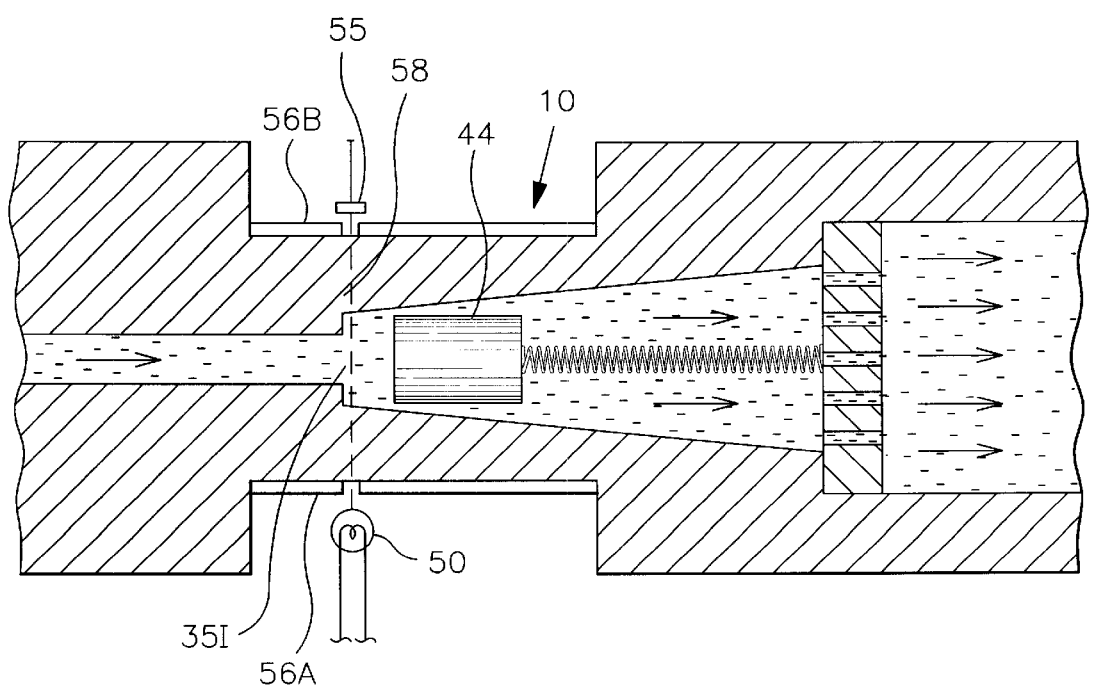
FIG. 2B is a schematic representation similar to that of FIG. 2 showing an alternate position of the stem body of the invention.

Referring now to FIGS. 2, 2A and 2B, an important component of the fluid flow monitoring device is shown as fluid conducting means 20. Preferably, the conducting means 20 is a conductor that has a clear conical wall 22 for advantageously visually ensuring that air is removed from the IV fluid path. In one preferred embodiment, the fluid conductor 20 extends between proximal and distal fluid conduits 30P and 30D. The case includes an inlet fluid conductor means 87P that connects the proximal conduit 30P to a source of intravenous fluid, preferably an IV bag 84, or a syringe (not shown) or an IV pumping device (not shown) well known to the field. An outlet fluid conductor means 87D connects the distal conduit 30D to an intravenous discharge device 88 that discharges the IV fluid to the patient's vein.

The conductor wall 22 has a conical shape having a slight wall divergence of approximately between 0.03 to 2.0 degrees, so that it is larger at its distal end. Preferably, a proximal and distal circular shoulders 33P and 33D are provided at the ends respectively of the conductor 20, the proximal shoulder 33P defining an inlet fluid orifice 35P, and the distal shoulder 33D defining an outlet orifice 35D.

In the preferred embodiment, an opaque stem body 40 for use with optically clear fluids, is a movable piston or plug element, and is provided within the the conductor 20. An alternate embodiment, to be discussed later, uses an optically clear stem body 40 for use with opaque fluids.

Figure 3:
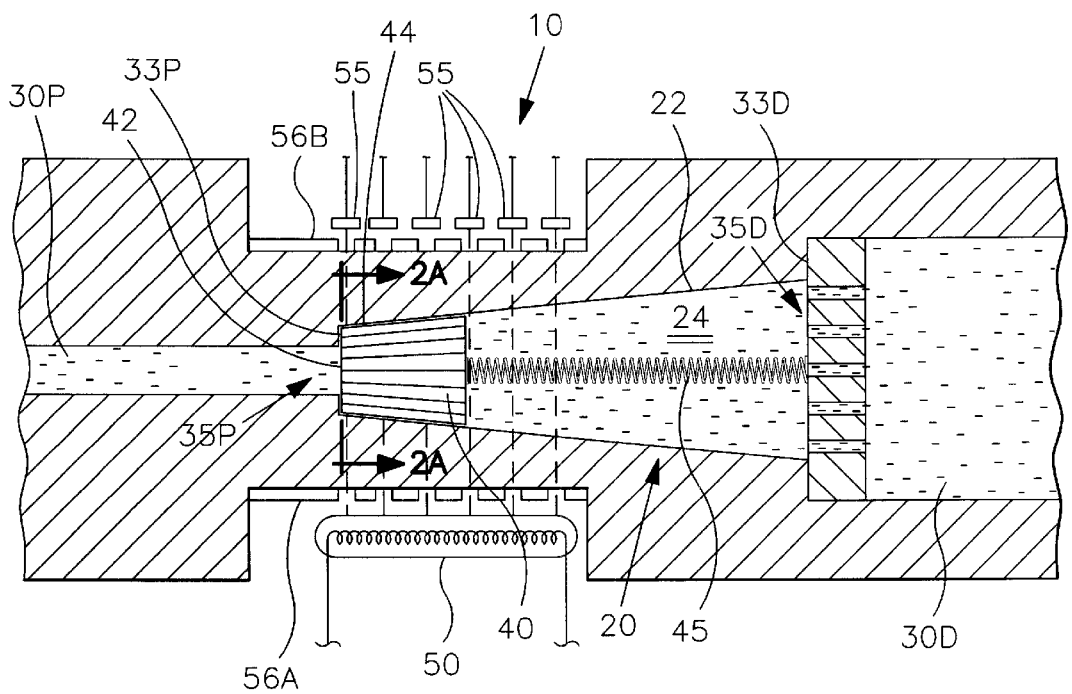
FIG. 3 is a schematic representation of a second prefered embodiment of the present invention of FIG. 1 shown as a flow rate indicator held within the case shown in FIG. 1, wherein some dimensions are shown exaggerated for better understanding of the principles involved, and particularly showing a flow conduit, inlet and outlet orifices, stem body, and light emitter and detector of the preferred embodiment.
Figure 3A:
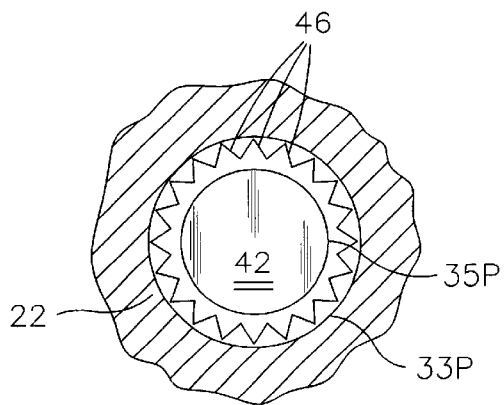
FIG. 3A is a cross-section view of the flow indicator switch taken along lines 3A—3A of FIG. 3 and particularly showing the preferred relationship between a proximal shoulder, the fluid conductor and an end of the stem body, wherein some dimensions are shown exaggerated for better understanding of the principles.
Figure 3B:
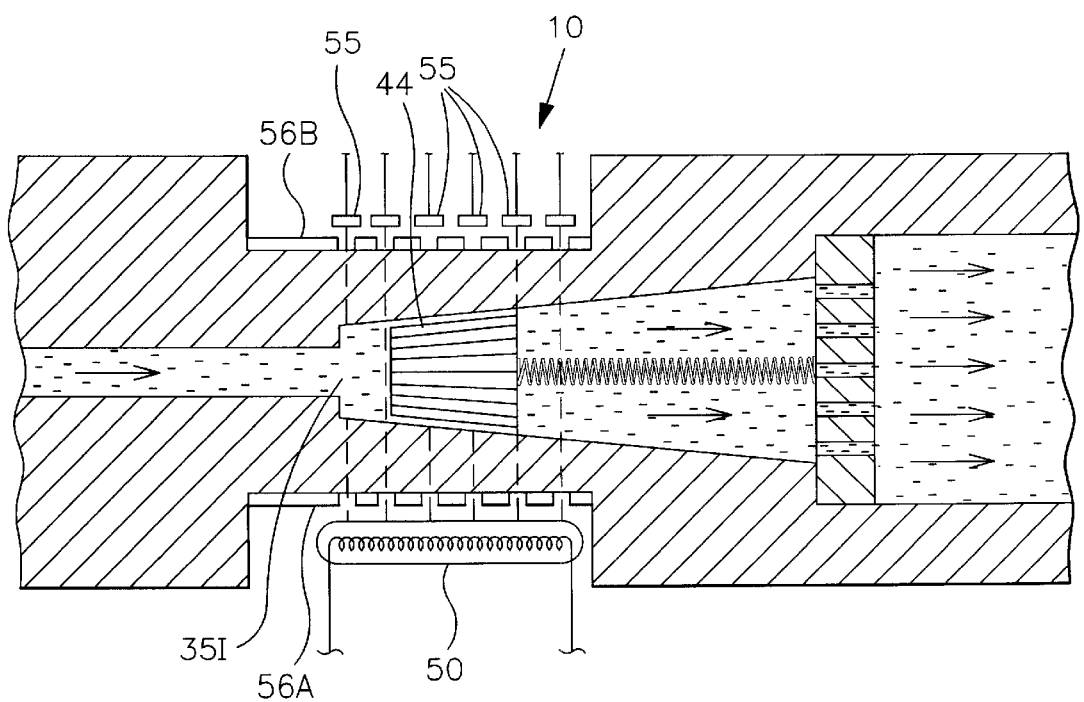
FIG. 3B is a schematic representation similar to that of FIG. 2 showing an alternate position of the stem body of the invention.
Figure 4:
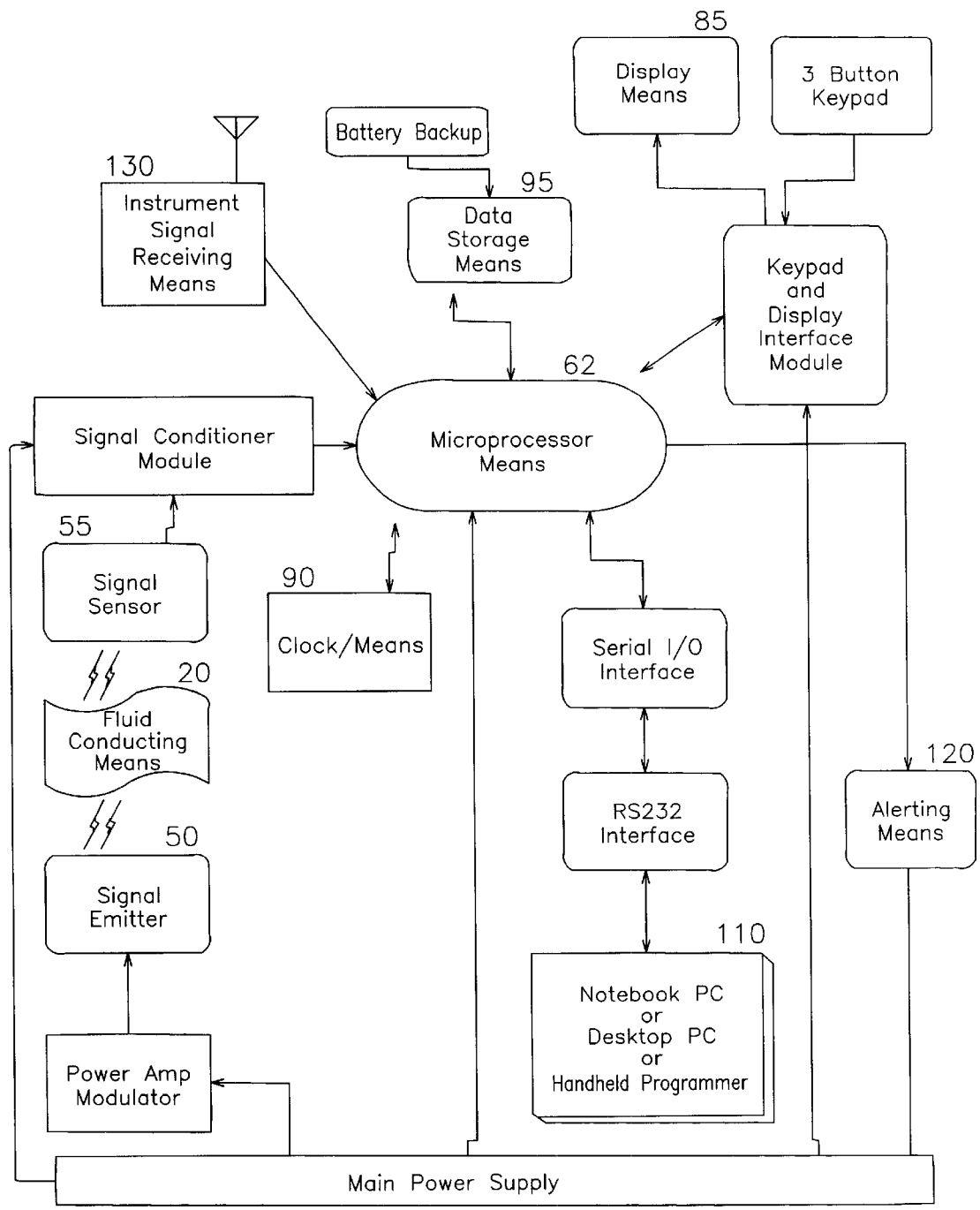
FIG. 4 is a general block diagram of an electronic circuit of the invention showing the preferred interconnections of various electrical elements of the invention.

In the preferred embodiment the body 40 has a volume of $6.8586 \times 10^{-3}$ cubic centimeters and a density of approximately 1.25 grams per cubic centimeter. As shown in FIG. 2, the stem body 40 preferably has a circular cross section and is slightly smaller in diameter than the conductor 20. When the stem body 40 is positioned at the proximal end of the conductor 20 abutting the proximal shoulder 33P, the stem body 40 does not engage any portion of the conical wall 22. The stem body 40 has a generally flat surface 42 at the end that contacts the proximal annular shoulder 33P, but does not form a tight seal with the shoulder. The stem body 40 may have a relatively smooth (FIG. 2A) or a ridged (FIG. 3A) outer surface 44 that provides a series of fluidic pathways 46 for conducting the fluid between the stem body 40 and the conical wall 22, thus providing improved conductance of the fluid. The surface 44 and fluid pathways 46 are shown in FIGS. 3 and 3A in an exaggerated manner. The preferred dimensional clearance between stem body 40 and the proximal shoulder 33P is about 0.0015 inches and this effective gap may often be accomplished by virtue of the natural texture or roughness of the surface of the materials without having to especially provide for grooved fluid pathways as shown in the aforementioned figures. The stem body is biased, preferably by means of a stem body biasing means 45 such as a spring, so that the surface 42 of the stem body 40 is urged in position against the proximal shoulder 33P, thus partially, but not fully, closing the fluid conductor 20 under static conditions. This partial closure allows at least some of the fluid to pass out of the conductor 20 in the direction away from the patient in the event that blood must be drawn from the patient or fluid must be removed from the line. It also allows for instantaneous equilibrium between pressure changes upstream or downstream of the stem body 40 in that upstream and downstream fluids are not mutually isolated. Occlusion of the flow path does not occur.

The spring constant of the biasing means 45 is preferably approximately 0.06 pounds per inch of deflection which means that the stem body 40 is displaced by a very slight flow of fluid into inlet 35P and out of outlet orifice 35D. It should be noted, however, that other spring constants and stem body masses may be selected for similar performance.

In one preferred embodiment shown in FIG. 2, the signal emitter-sensor means 52 consists of a signal emitter 50 positioned outside of the conductor 20, lateral to the stem body 40, and a single signal detector 55 positioned directly across from the emitter 50, on the opposite side of the conductor 20. As shown in FIG. 2, the left-hand side edge of the detector 55 is aligned with the proximal shoulder 33P and the base of the stem body 40. A masking means is positioned between the emitter-sensor means 52 and the stem body 40. In one preferred embodiment, the masking means 52 consists of one mask 56A positioned between the signal emitter 50 and the stem body 40, and another mask 56B placed between the detector 55 and the opposing side of the stem body 40. Preferably, both masks 56A and 56B have tiny openings that are aligned in corresponding pairs in opposition across the fluid conductor. In the preferred embodiment, these openings are between 0.003 to 0.030 inches in diameter depending upon the power of the emitter 50 and the sensitivity of the detector 55 These openings in the masks 56A and 56B restrict signal travel from the emitter 50, to a narrow signal path 58 across the fluid conductor 20, thereby focusing the signal. As seen in FIG. 2, when the stem body 40 is in position against the proximal shoulder 33P, the signal path 58 between the emitter 50 and the detector 55 is fully blocked by the opaque stem body 40, the signal is prevented from fully reaching the signal detector 55. However, as seen in FIG. 3, when the stem body 40 moves away from the proximal shoulder 33P, the signal path 58 is provided. Thus, any change in position of the stem body 40 within fluid conductor 20 is easily determined by whether the signal path 58 is blocked or not.

Although FIGS. 2 and 2B show an embodiment with a single signal detector 55, the signal emitter-sensor 52 may also consist of a linear sequence of independent signal emitters 50 and sensors 55 as shown in FIG. 3. In this alternative manner, an IV line with a constant flow, such as those used for KVO or "Keep Vein Open" applications, may be monitored for a meaningful change in flow rate. In the preferred embodiment, the signal emitter-sensor means 52 preferably emits and senses light signals in infrared wavelengths, although it is by no means limited to such use.

As mentioned previously, in the preferred embodiment the stem body 40 is opaque in order to block the passage of the signal from the emitter 50 to the detector 55 when used with optically clear fluids. In certain instances however, a patient may receive IV fluids such as blood products or feeding solutions, that are not optically clear. The optical properties of these opaque solutions naturally attenuate light passing through them. This attenuation is proportional to the length of distance that the light must pass through the fluid. Therefore, an alternative embodiment of the stem body 40 uses a clear plastic which then limits the attenuation to that which occurs over a few thousandths of an inch. In this manner, the electronics may be modified to receive an optical signal for "no-flow" conditions and an opaque or blocked signal for "flow" conditions.

The processor circuit 60 of the intravenous system may use a digital microprocessor chip to provide a logic program for interfacing the device into a therapeutic program of IV infusion and other medications. The circuit 60 preferably provides a means for using electrical signals from the detector 55 to store IV fluid flow event information. Intermittently, it is possible that non-fluidic events, such as the motion of a patient, may cause spurious signals due to minor displacements of the stem body 40. Testing has shown that these spurious signals are of short duration, such as a fraction of a second. The case 80 houses the processor circuit 60 which also includes logic for determining minimum "Flow On" time periods and intervals to remove most spurious signals from the log of flow events stored in memory.

The processor circuit 60 preferably includes a processor means 62, clock means 90 and a data storage means 95 interconnected so as to enable the processor circuit 60 to gather and record information concerning the infusion such as the time of day at start, time of day at stop, and time of day at change in IV flow rate with each associated flow rate change. The processor circuit 60 also preferably includes a parameter measuring instrument signal receiving means 130, which, in one preferred embodiment, consists of an analog-to-digital circuit, an amplifier and a jack. A variety of different measuring instruments (not shown), such as a scale or a thermometer, may be quickly and easily interconnected with the instrument signal receiving means 130 so that parameters pertinent to the patient's (pulse, blood pressure, body temperature, weight, etc.) condition may be easily and effectively monitored. The data received by the signal receiving means 130 is stored in the data storage means 95.

All data stored in the data storage means 95 may either be visually accessed by the patient at the display means 85 of the processor circuit 60 contained within the case 80, or, alternately, the circuit 60 may also include a communication means 100 that enables communication between the circuit 60 and a computer system 110. The communication means 100 may be either a hardwire or a wireless device of the type well known in the art. From the computer system 110, recorded data may be quickly uploaded and viewed.

A variety of pertinent information, such as oral medication schedule, may also be programmed into the computer 110 as desired. The processor circuit 60 of the present invention preferably includes an alerting means 120 for reminding the patient when to take oral medications or begin an IV infusion, for alerting the patient when the recorded body temperature is too high, fluid flow rate is too low, etc. To accomplish this, the desired information, as for example the times of day at which infusions should begin, is programmed into the computer 110. When the time recorded by the clock means 90 corresponds with the preprogrammed infusion times, the alerting means 120 alerts the patient by producing an audible alarm, vibrating or any other such means. In the same manner, a range of preferred fluid flow rates may be preprogrammed into the computer 110, and when the recorded flow rate during a infusion does not fall within the specified range, the alerting means is actuated.

Thus, in use, the proximal conduit 30P is connected to an IV bag or other fluid source, and the distal conduit 30D connects to an intravenous discharge device interconnected with a vein. Both conduits 30P and 30D and the conductor 20 are filled with IV fluid and deaired prior to attaching to the patient, and the stem body 40 is nominally positioned against the proximal shoulder 33P indicating a no flow condition. The system remains static until flow from the IV bag or other fluid source is activated and the stagnation pressure due to fluid motion against the stem body 40 increases. The force on stem body 40 overcomes the restoring force of the biasing means 45, causing stem body 40 to move away from the proximal shoulder 33P. This allows fluid which flows from the conduit 30P and through the inlet orifice 35P to be immediately sensed. The force of the fluid flow moves stem body 40 to a position within the fluid conductor 20 where a state of dynamic equilibrium is achieved between the force of fluid against stem body 40 and the restoring force. As stem body 40 moves further toward the distal end of the fluid conductor 20, as is typical at higher flow rates, the annular flow path area between the stem body 40 and the conical conductor wall 22 becomes larger, thereby increasing flow conductance in the conductor 20. Therefore a nonlinear relationship is developed between stem body displacement and conductance such that backpressure is minimized very quickly.

In particular, when the stem body 40 is positioned against the proximal shoulder 33P, as shown in FIG. 2, it blocks the signal from arriving at the leftmost edge of sensor 55. This leftmost edge of sensor 55 is particularly of interest in establishing if fluid in the system is static, or is flowing. Further, the signal reaching the leftmost edge of sensor 55 does not have to saturate the photodector means in signal sensor 55. In the preferred embodiment, a signal of about 300 millivolts is generated when the sensor 55 is fully saturated when both tiny openings 56A and 56B are fully exposed. However, an almost minuscule change in position of stem body 40 will cause a smaller change in voltage from 0.0 millivolts (totally opaque) to 0.5 millivolts because the leftmost edge of sensor 55 is partially illuminated. This smaller change is voltage is used to determine that fluid motion has commenced or ceased. Thus the signal induced by the leftmost edge of sensor 55 is used in the preferred embodiment to determine the "flow ON/OFF" time periods. The detector 55 signals are used in the processor circuit 60, thereby to log start and stop of fluid flow.

While the invention has been described with reference to a preferred embodiment, it is to be clearly understood by those skilled in the art that the invention is not limited thereto. Rather, the scope of the invention is to be interpreted only in conjunction with the appended claims.

What is claimed is:

1. A fluid flow monitoring device comprising:

a transparent fluid conducting means enclosing a stem body movable along the fluid conducting means and biased against a proximal interior shoulder of the fluid conducting means, said shoulder defining a fluid inlet; and a signal emitter-sensor means positioned externally to the fluid conducting means for transmitting a signal across the fluid conducting means from an emitter of the emitter-sensor means, to a sensor of the emitter-sensor means, such that with the stem body in a first stem body position within the fluid conducting means, the signal is blocked, and with the stem body in a second stem body position within the fluid conducting means, the signal is not blocked, said second stem body position adapted by the stem body as a result of a fluid flow within the conducting means wherein the fluid flow is sensed by the emitter-sensor means as the stem body moves.

2. The device of claim 1 further including a masking means interposed between the emitter-sensor means and the stem body, the masking means adapted for focusing the signal.

3. The device of claim 1 wherein the fluid conducting means is of a conical shape oriented such that resistance to the fluid flow by the stem body when in the second position is less then when in the first position.

4. The device of claim 1 further including a processor circuit in communication with the signal emitter-sensor means, and comprising a processor means, a clock means, a data storage means, a visual display means, and an alerting means, all interconnected, so as to enable the circuit to identify a time data, and display a fluid flow state, type of medication scheduled, and time of next scheduled medication.

5. The device of claim 4 further including parameter measuring instrument signal receiving means.

6. The device of claim 4 further including a communication means interconnecting the processor circuit with a computer, the computer being programmed to record and display data.

7. The device of claim 6 wherein the communication means is at least one electrically conducting path.

8. The device of claim 6 wherein the communication means is a wireless device.

9. The device of claim 4 further including an alerting means for signaling a user when recorded data corresponds with preprogrammed data.

10. The device of claim 9 wherein the alerting means produces an audible noise.

11. The device of claim 9 wherein the alerting means produces a mechanical vibration.

12. The device of claim 1 wherein the stem body has a circular cross-section with one end thereof providing a generally flat surface, said surface not forming a tight seal when in contact with the proximal shoulder.

13. The device of claim 12 further including a wristwatch size case encompassing the processor circuit, said case positionable for viewing and further including a fluid inlet conducting means, and a fluid outlet conducting means.

14. The device of claim 1 wherein the signal emitter-sensor means comprises a linear sequence of independent sensors, movement of the stem body blocking at least one of said sensors, such that the position of the stem body is known at each position of the stem body within the conducting means.

15. The device of claim 1 wherein the stem body includes a generally circular outside surface, the surface providing a plurality of fluidic pathways for conducting the fluid between the stem body and the conical wall of the conducting means providing improved conductance of the fluid therebetween.

16. The device of claim 1 wherein the moveable stem body is optically clear.

17. The device of claim 16 wherein the fluid flow is optically opaque, the fluid blocking the signal reception in at least one position of the stem body, the stem body displacing the fluid flow in at least one other position of the stem body to allow the signal to be received.

18. The device of claim 1 wherein the stem body and the fluid conducting means are shaped, finished and contoured so that the static line pressure of the fluid is a constant at all points in the device and irrespective of the position of the stem body within the conducting means.

* * * * *